United States Patent
Sauer et al.

[11] Patent Number: 6,009,142
[45] Date of Patent: Dec. 28, 1999

[54] PRACTICAL CONE BEAM IMAGE RECONSTRUCTION USING LOCAL REGIONS-OF-INTEREST

[75] Inventors: Frank Sauer; Supun Samarasekera, both of Princeton; Kwok Tam, Edison, all of N.J.

[73] Assignee: Siemens Corporate Research, Inc., Princeton, N.J.

[21] Appl. No.: 09/052,415

[22] Filed: Mar. 31, 1998

[51] Int. Cl.[6] .......................................... A61B 6/03
[52] U.S. Cl. .................... 378/15; 378/4; 378/901
[58] Field of Search .................. 378/4, 15, 901

[56] References Cited

U.S. PATENT DOCUMENTS 5,257,183  10/1993  Tam ..................... 364/413.19

OTHER PUBLICATIONS

U.S. Patent Application No. 08/940,489 filed Sep. 30, 1997 to Sauer et al. entitled "A Reduction of Hitlist Size in Spiral Cone Beam CT by Use of Local Radon Origins".

Primary Examiner—David Vernon Bruce
Attorney, Agent, or Firm—Lawrence C. Edelman

[57] ABSTRACT

A method and apparatus of operating a CT imaging apparatus having a cone beam radiation source and a 2D detector arrangement, for exactly reconstructing an image of a 3D region of interest (ROI) in an object. Measurement data acquired by the 2D detector is processed to develop sub-sets of Radon data. Each of the sub-sets of Radon data is targeted for reconstructing a corresponding local 2D ROI in a 2D parallel projection of the object. Accordingly, after a sub-set of Radon data is completely developed, it is subjected to a first inversion processing step for developing the corresponding local 2D ROI. Multiple ones of the local ROIs are then grouped together and subjected to a second inversion processing step to develop an image reconstruction of a part of the 3D ROI in the object.

27 Claims, 6 Drawing Sheets

→ CONVERSION PROCESSING — 502

⇓

$RD_{1,1}$ $RD_{1,2}$ ... $RD_{1,N}$

⋮

$RD_{M,1}$ $RD_{M,2}$ ... $RD_{M,N}$

$ROI_{1,1}$ $ROI_{1,2}$ $ROI_{1,N}$ $ROI_{M,1}$ $ROI_{M,2}$ $ROI_{M,N}$

PRACTICAL CONE BEAM IMAGE RECONSTRUCTION USING LOCAL REGIONS-OF-INTEREST

BACKGROUND OF THE INVENTION

1. Field of the Invention

The present invention relates generally to computed tomographic (CT) imaging using a cone beam radiation source for performing an exact image reconstruction of an object, and more specifically to a method and apparatus for performing image reconstruction by individually processing multiple sub-sets of Radon data. Each of the sub-sets of Radon data is targeted for reconstructing a local 2D region-of-interest (ROI) in a 2D parallel projection of the object, and after multiple local 2D ROI's are reconstructed they are jointly processed for developing a portion of the image reconstruction of the object.

2. Description of the Background Art

Recently a system employing cone beam geometry has been developed for three-dimensional (3D) computed tomographic (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After completion of measurement data acquisition, the measurement data is processed for reconstructing a 3D image of the object.

However, before one can perform accurate 3D imaging of the object (or a region of interest in the object), one needs a complete set of measurement data, i.e., one needs to satisfy completeness criteria. Basically, what is required is that planes, referred to hereinafter as "integration planes", that are within the field of view of the radiation source that pass through the object, or 3D region of interest of the object, and also intersect the scan path at one or more locations, develop measurement data that must be processed to accurately perform the image reconstruction. These criteria are well known, and are described in detail, for example, in U.S. Pat. No. 5,383,119 entitled METHOD AND APPARATUS FOR ACQUIRING COMPLETE RADON DATA FOR EXACTLY RECONSTRUCTING A THREE-DIMENSIONAL COMPUTERIZED TOMOGRAPHY IMAGE OF A PORTION OF AN OBJECT RADIATED BY A CONE BEAM SOURCE issued on Jan. 17, 1995, hereby incorporated by reference. This patent notes that the acquired sets of measurement data are complete only if they can be processed so as to develop Radon data of sufficient density in a so-called "region of support" (a region which topologically corresponds to the field of view occupied by the region of interest of the object in real space), which can subsequently be processed to reconstruct the object with the desired resolution, and without artifacts. Typically, sufficient Radon data is acquired by exposing the entire object within the field of view to the radiation source.

Sufficient filling of the Radon space by cone beam CT apparatus having various scanning trajectories (paths) and using an area detector which is smaller than the region of interest being imaged, are known for performing an exact image reconstruction. For example, FIG. 1 herein illustrates the scanning technique disclosed in U.S. Pat. No. 5,463,666 entitled HELICAL AND CIRCLE SCAN REGION OF INTEREST COMPUTERIZED TOMOGRAPHY issued Oct. 31, 1995. A region of interest portion 10 (dark shading) of an object 12 can be imaged without blurring or artifact introduction by providing a scan path 14 consisting of a central spiral portion 16 having a circle portion $18_U$ and $18_L$ at upper and lower ends, respectively, of the spiral portion which are level with upper and lower boundaries of the region of interest of the object. The switch from a spiral scan path to a circular scan path is necessary in order to obtain complete cone beam data at the upper and lower boundaries of the region of interest without causing blurring caused by imaging portions of the object not within the region of interest, as described in greater detail in the fore-noted U.S. Pat. No. 5,463,666.

Although the above and other techniques have been useful, they require scan paths which have abrupt shifts in movement. Such abrupt shifts in scan movement are undesirable in that they either subject the patient to undesired jostling, or subject the imaging system equipment to extra mechanical stress. It would be desirable to only provide a smoothly changing scan path.

Furthermore, it is noted that compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source, and complex processing of the acquired measurement data is required to develop appropriate Radon transform data. Such processing for exactly reconstructing an image of the object typically, comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

Although the theory for exactly reconstructing an image using cone beam measurement data is generally known, such as from the US patents noted above, a practical implementation of the processing turns out to be quite problematic. Not only is the amount of measurement data to be processed very large and rapidly acquired in accordance with a timing that is mainly determined by the geometry of the scan path, but, as noted above, the calculations required on the acquired data are quite complex. The most computationally expensive part of the object reconstruction is the calculation of the Radon derivative data (steps 1 and 2 noted above). Typically one needs to calculate about $100 \times 10^6$ line integral derivatives during object reconstruction. Since each line integral derivative requires the calculation of two single line integrals (because one uses the difference between two closely spaced line integrals to calculate a single line integral derivative) $200 \times 10^6$ single line integral calculations are required. However, before one can even begin to perform these line integral derivative calculations, one has to compute for each Radon sample which source positions will provide the measurement data that must be processed, and determine the extent of the lines on the measurement data along which the integration must be performed. These latter determinations involve highly nonlinear calculations and are therefore computationally costly and time consuming, undesirably delaying an image reconstruction of the object.

Figure 2:
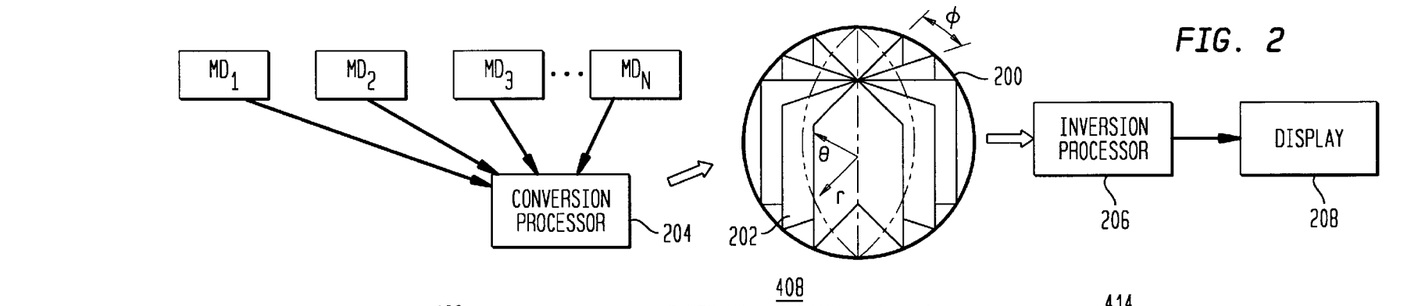

FIG. 2 herein generally illustrates the conventional prior art technique for processing the acquired measurement data for image reconstruction. As shown, sets of measurement data $MD_1$, $MD_2$, $MD_3$ ... $MD_N$ obtained at corresponding source positions $SP_1$, $SP_2$, $SP_3$ ... $SP_N$ of the radiation source along scan path 16, are sequentially processed to develop a sufficient amount of Radon data to uniformly fill up a Radon space 200 defined by a spherical coordinate system (r, θ, ψ), with sufficient density to allow image reconstruction of object 16 at a desired resolution and without artifacts. The Radon data is developed at a large number of radially arranged polar grid points on a plurality of ψ-planes 202, by conversion processor 204 operating according to the above steps 1) and 2). As previously noted, the development of the Radon data is not complete until measurement data has been obtained from all the source positions of the scan path, including those that lie on both of the top and bottom circle portions. Only after the Radon data is completely developed is it subjected to inverse transform processing according to the above step 3), via processor 206, and then passed to a display 208 for visualizing the image reconstruction.

The consequence of the above is two-fold, 1) image reconstruction is undesirably delayed until the entire 3D region-of-interest of the object is scanned by the source/detector arrangement, and 2) a very large amount of system memory must be allocated for storage of all of the calculated Radon data, since inversion processing uses the global Radon transform of the entire 3D region-of-interest of the object.

It would be desirable to reduce the time delay before which the user can begin to obtain image reconstruction, and at the same time, reduce the data storage requirements of the imaging system. Furthermore, it would be desirable that these goals be achieved in a practical manner that doesn't significantly increase the complexity or degrade the performance of the exact cone beam image reconstruction.

SUMMARY OF THE INVENTION

A method and apparatus of operating a CT imaging apparatus having a cone beam radiation source and a 2D detector arrangement, for reconstructing an image of a 3D region of interest (ROI) in an object. Measurement data acquired by the 2D detector is processed to develop sub-sets of Radon data. Each of the sub-sets of Radon data is targeted for reconstructing a corresponding local 2D ROI in a 2D parallel projection of the object. Accordingly, after a sub-set of Radon data is completely developed, it is subjected to a first inversion processing step for developing the corresponding local 2D ROI. Multiple ones of the local ROIs are then grouped together and subjected to a second inversion processing step to develop an image reconstruction of a part of the 3D region of interest in the object.

The invention provides benefits relating to a more simplified scan path, reduced memory requirements, and a reduced time delay from the beginning of measurement data acquisition to the beginning of the display of image reconstruction.

DETAILED DESCRIPTION OF THE PREFERRED EMBODIMENTS

Figure 3:
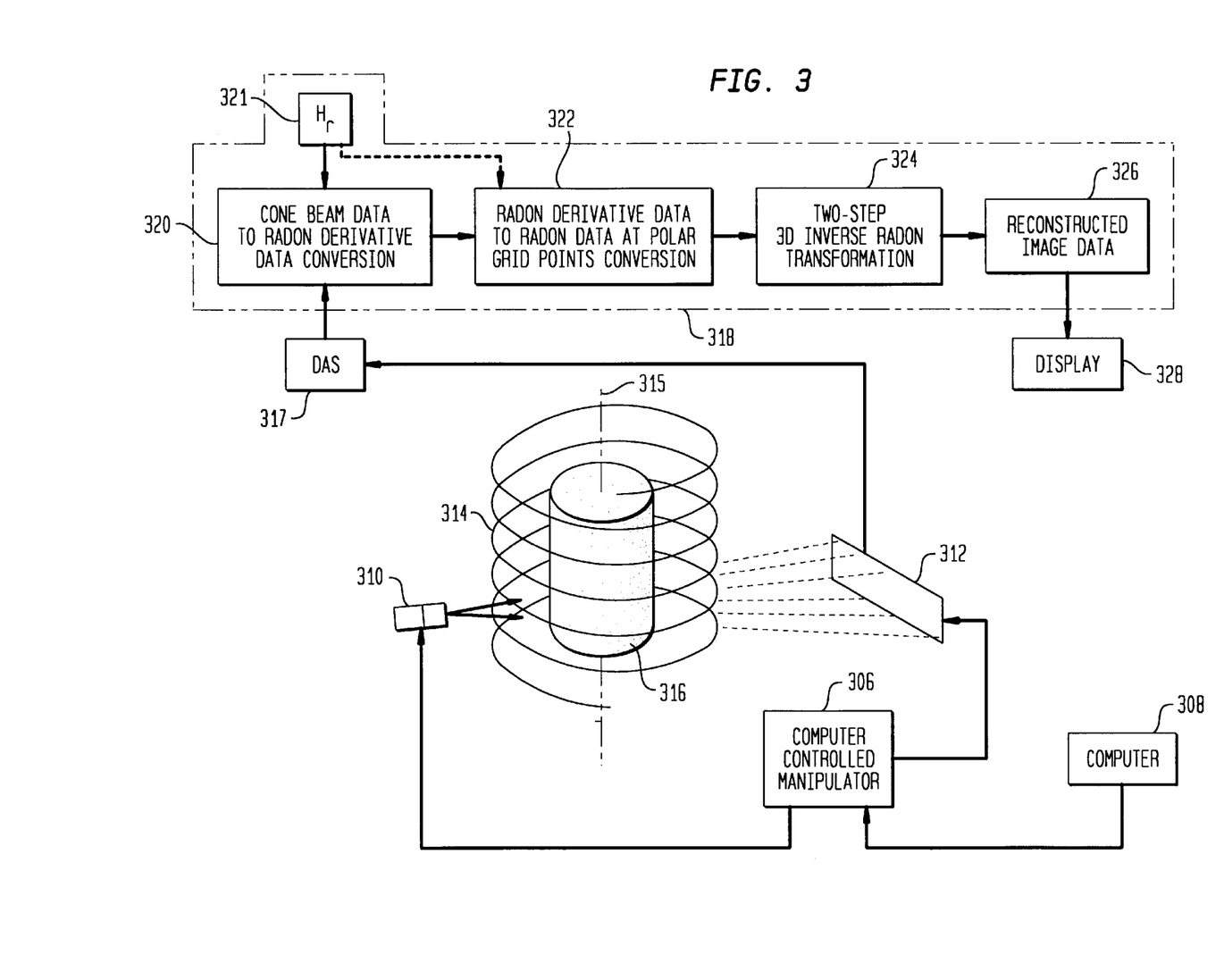
FIG. 3 is a block diagram and simplified perspective illustration showing the imaging of an object using a cone beam imaging apparatus for acquiring and processing measurement data in accordance with the principles of the present invention.

FIG. 3 illustrates a cone beam 3D CT imaging apparatus useful for processing acquired measurement data in accordance with the principles of the present invention. As will become apparent, the illustrated imaging apparatus is constructed and operates substantially in accordance with same principles described in the forenoted U.S. Pat. Nos. 5,257,183 and 5,446,776, except as to be specifically described later with respect to the source scanning path and implementation of image reconstruction processing in accordance with the present invention.

As shown in FIG. 3, a computer controlled manipulator 306, in response to control signals from an appropriately programmed computer 308, cause a source 310 of a cone or pyramid shaped beam of energy (such as x-rays) and a two-dimensional pixelated detector array 312 to cooperate (scan) at a plurality of discrete, sequentially occurring adjacent source positions, along a pre-defined source scanning path. In the illustrated embodiment the scanning path is shown as a spiral scan path 314 centered on a predetermined axis 315 of an object 316. Other types of scan paths that encircle and traverse object 316 can also be used, however, as will become apparent later, a scan path 314 exhibiting a high degree of symmetry in its parallel projections is preferred.

As a result of the source/detector cooperation under control of computer 306 and manipulator 308, at each of the source positions x-ray energy passes through the field of view of the imaging apparatus, is attenuated by object 316, and a set of measurement data corresponding to the sensed x-ray energy falling on the elements (pixels) within detector 312 are developed. The sets of measurement data are then supplied to a data acquisition system (DAS) 317 which, like the previously described portions of FIG. 3, may operate in a fashion well known to those of ordinary skill in this technology for digitizing and storing of the acquired measurement data.

It is to be noted that alternatively, and equivalently, object 316 could be rotated and translated to cause scanning by a fixed position source and detector, that the rotation could be provided by the source and detector and the translation could be accomplished by the object, and that scanning can be accomplished in a continuous or stepwise manner. Even furthermore, although source 310 is shown as an x-ray source, other types of imaging energy might be useful, such as neutrons, positrons, etc.

As previously noted, in accordance with the prior art techniques it was necessary to completely scan the entire 3D volume of the object's ROI before complete Radon data would be developed. However, as will be explained next, operation of apparatus in accordance with the present invention allows use of the measurement data that results from scanning only a partial volume of the object to develop complete sub-sets of the Radon data, thereby allowing Radon inversion processing to begin much sooner, and greatly reducing the storage requirements for the Radon data.

The measurement data from DAS 317 are supplied to a buffer memory and image reconstruction processor 318, which may be a computer programmed to perform various data conversions, that processes the measurement data so as to exactly reconstruct an image of the scanned object in accordance with the processing steps generally illustrated by blocks 320 to 324.

At block 320 the measurement data is processed so as to be converted to Radon derivative data. A spherical coordinate system (r, θ, ψ) defining a Radon space partitioned by a plurality of vertically oriented co-axial ψ-planes, is used to facilitate a subsequent inversion processing of the Radon data. Conversion of measurement data to Radon data is accomplished, in general, using the techniques described in the forenoted U.S. Pat. No. 5,257,183. However, as will be described in greater detail later, in a preferred embodiment of the present invention, instead of performing all of the conversion calculations "on the fly", it is best to make use of the a pre-calculated "relative hitlist" for speeding up the conversion. The construction and operation of such a hitlist is described in detail U.S. patent application Ser. No. 08/940, 489, entitled A REDUCTION OF HITLIST SIZE IN SPIRAL CONE BEAM CT BY USE OF LOCAL RADON ORIGINS, filed Sep. 30, 1997, incorporated herein by reference.

Briefly, this patent application describes the use a "relative" hitlist ($H_r$) of pre-calculated image reconstruction processing information to greatly aid the conversion of measurement data to Radon data. In general, the hitlist contains data conversion processing information that is determined primarily by geometric parameters of the imaging apparatus and are therefor already determined before its imaging operation, such as the pitch and other parameters of the source/detector scan path, the object dimensions, the detector resolution, and the sampling of the scan path and the Radon space. These parameters define the line integrals which need to be calculated in the measurement data to develop the desired samples of the Radon data. Thus, the hitlist indicates the correspondence between points in Radon space and the source positions that contribute thereto, parameters that define the line integrals that need to be calculated in the measurement data acquired at each of the source positions, as well as other information useful for image reconstruction processing. Typically the imaging system manufacturer will pre-calculate the hitlist information and store it in a memory, such as database 321. The hitlist information is used during run-time (imaging) operation of the apparatus to assist the conversion processing of the acquired measurement data into the many samples of Radon derivative data needed to fill up the region of Radon support for proper reconstruction of the object. Furthermore, due to a symmetry that is induced in the subsequent Radon inversion processing, the stored information for only one of the Radon space ψ-planes can be used for calculating Radon derivative data for all of the other Radon space ψ-planes. Accordingly, the memory requirements for the hitlist are greatly reduced. Furthermore, use of a hitlist results in improvement of the speed and efficiency of the image reconstruction processing as compared to conversion processing without use of a hitlist.

As will be described in detail later, in the present invention the use of the hitlist technique is particularly advantageous in that it provides an efficient way to target the measurement data to develop specific predetermined sub-sets of the Radon derivative data.

At block 322 the Radon derivative data is converted to Radon data at polar grid points on ψ-planes of a spherical coordinate system using, for example, the technique described in detail in conjunction with FIG. 5 of the forenoted U.S. Pat. No. 5,446,776. Briefly, as described therein, the Radon derivative data from block 320 is converted to Radon derivative data at equally spaced polar grid points using nearest neighbor or interpolation techniques, and then summed to develop the Radon data at equally spaced polar grid points. The hitlist of reconstruction processing information stored in database 321 preferably also provides precalculated information during this portion of the reconstruction processing, such as weighting information used for interpolation processing (as indicated by a dashed line from block 321 to block 322), thereby further improving the speed and efficiency of this portion of the reconstruction processing.

At block 324 the Radon data is subjected to inverse 3D Radon transformation in accordance with a two-step process. The image data developed thereby is stored at block 326 and then fed from reconstruction processor 318 to a display 328, which may operate in known fashion, to provide a 3D CT view of object 316.

Figure 4:
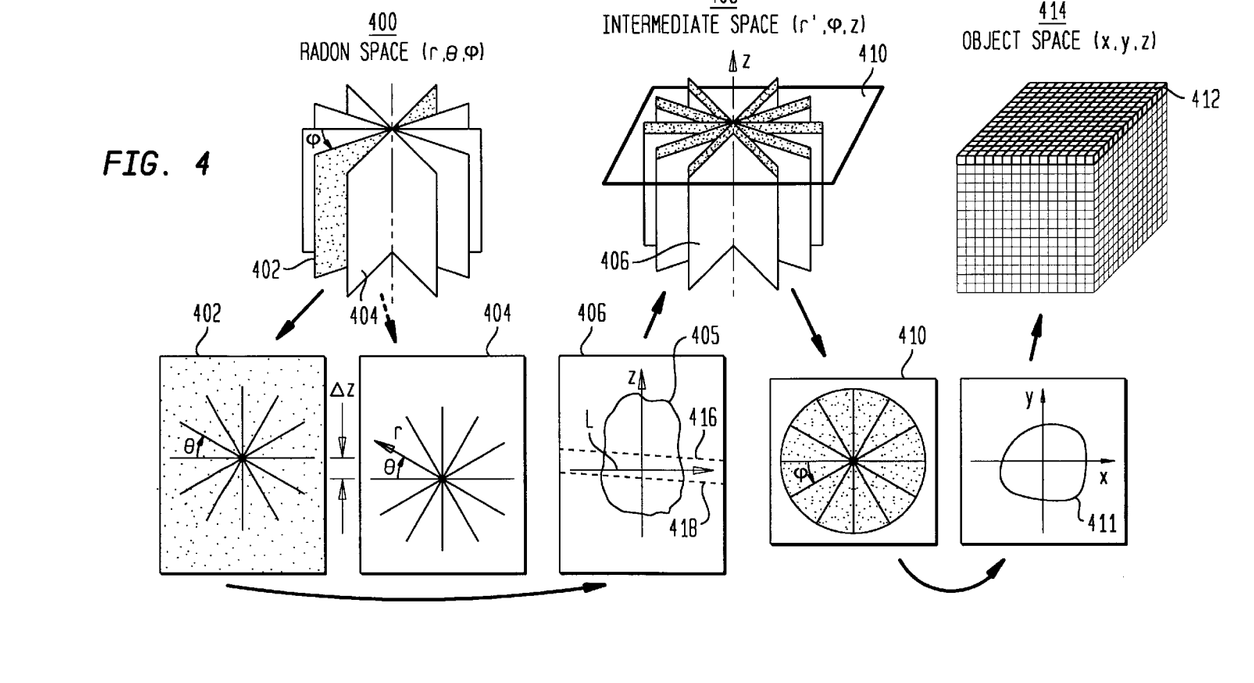
FIG. 4 illustrates a two-step process for 3D Radon transform inversion.

FIG. 4 illustrates the two-step Radon inversion processing carried out by block 324, which is generally known and described, for example, in the forenoted U.S. Pat. No. 5,257,183. Briefly, one starts with the Radon data samples supplied by block 322, distributed in a Radon space 400 that is defined by a spherical coordinate system (r,θ,ψ). Two ψ-planes 402 and 404 of a plurality of vertically oriented coaxial ψ-planes that partition Radon space 400 are illustrated. Each ψ-plane has the Radon data samples arranged on a polar grid, such as the grids shown in ψ-planes 402 and 404. As will be apparent later, the origin of the sample grid of each of the ψ-planes is permitted to be independent of one another.

In the first inversion processing step, 2D Radon inversions are performed on the Radon data in each of the (ψ-planes using a procedure such as filtered backprojection, to develop a 2-D parallel projection of a 3D ROI of the object, such as projection image 405, for the corresponding viewing direction, i.e., a corresponding ψ-plane 406 sampled in an intermediate space 408 defined by cylindrical coordinates (r', ψ, z). The second inversion processing step, using a procedure such as filtered backprojection, operates in intermediate space 408 on the data in horizontal planes (z-slices). The result is the determination of a 2D image 411 in a corresponding z-plane 412 sampled in an object space 414 defined by Cartesian coordinates (x,y,z). The second inversion processing step is repeated so as to operate on successive horizontal z-planes of intermediate space 408, thereby reconstructing an image of the object z-slice by z-slice.

As previously noted, in the preferred embodiment of the invention a relative hitlist is used, resulting in ψ-planes 402, et seq. having independent, i.e. local, Radon origins. Although use of the relative hitlist results in significant speed and efficiency advantages, it also results in a shifted local origin for each ψ-plane, as shown by the delta-z amount in FIG. 4. Accordingly, before performing the second inversion processing step, it is necessary to take the delta-z shifted amount into account when assembling ψ-planes 406 so that the z-slice portions of the 2D ROI images 405 over the many ψ-planes making up space 408 are consistent, i.e., pertain to the same z-portion of a global coordinate system in space 408.

The present inventors realized that when the inversion of the 3-D Radon data is performed with the 2-step process described in FIG. 4, not only can each (plane of Radon space 400 have its individual Radon origin, but that the 2D projection images developed thereon can also be "local", i.e., if only a portion of images 405 could be developed at a time, such as that portion L between dashed lines 416 and 418, called hereinafter a local ROI, then multiple local ROI's could be pieced together to reconstruct image 405. Although it is not required that different local ROI can be derived from a unique global 3D ROI of the object, each local ROI does correspond to a 3D partial volume of the object, and therefore a set of local ROIs can contain and be used to reconstruct a 3D ROI of the object.

At first this thought of the development of local 2D projection images may not seem significant, but in fact, it allows the use of a simpler scan path, reduces the time delay before which reconstructed images can start to be displayed, and greatly reduces the memory requirements needed for image reconstruction.

More specifically, it is now possible, instead of developing a global Radon transform for the entire 3D ROI of the object, to develop sub-sets of Radon data. Each sub-set targets the reconstruction of a corresponding local ROI of the object's parallel projection. There are one or more local ROIs on each ψ-plane. Once the Radon data set needed for reconstructing a given local 2D ROI is used, it can be discarded, resulting in a very significant decrease in the system memory requirements needed for image reconstruction. Furthermore, the size of the relative hitlist 321 used for conversion of the measurement data to Radon derivative data, as described in the forenoted patent application Ser. No. 08/940,489, can also be greatly reduced, since the image processing information in the relative hitlist can be re-used, in a relative sense, not only for developing the Radon data for multiple local ROIs in a given ψ-plane 406, but for all local ROIs in all of the ψ-planes of intermediate space 408.

Figure 1:
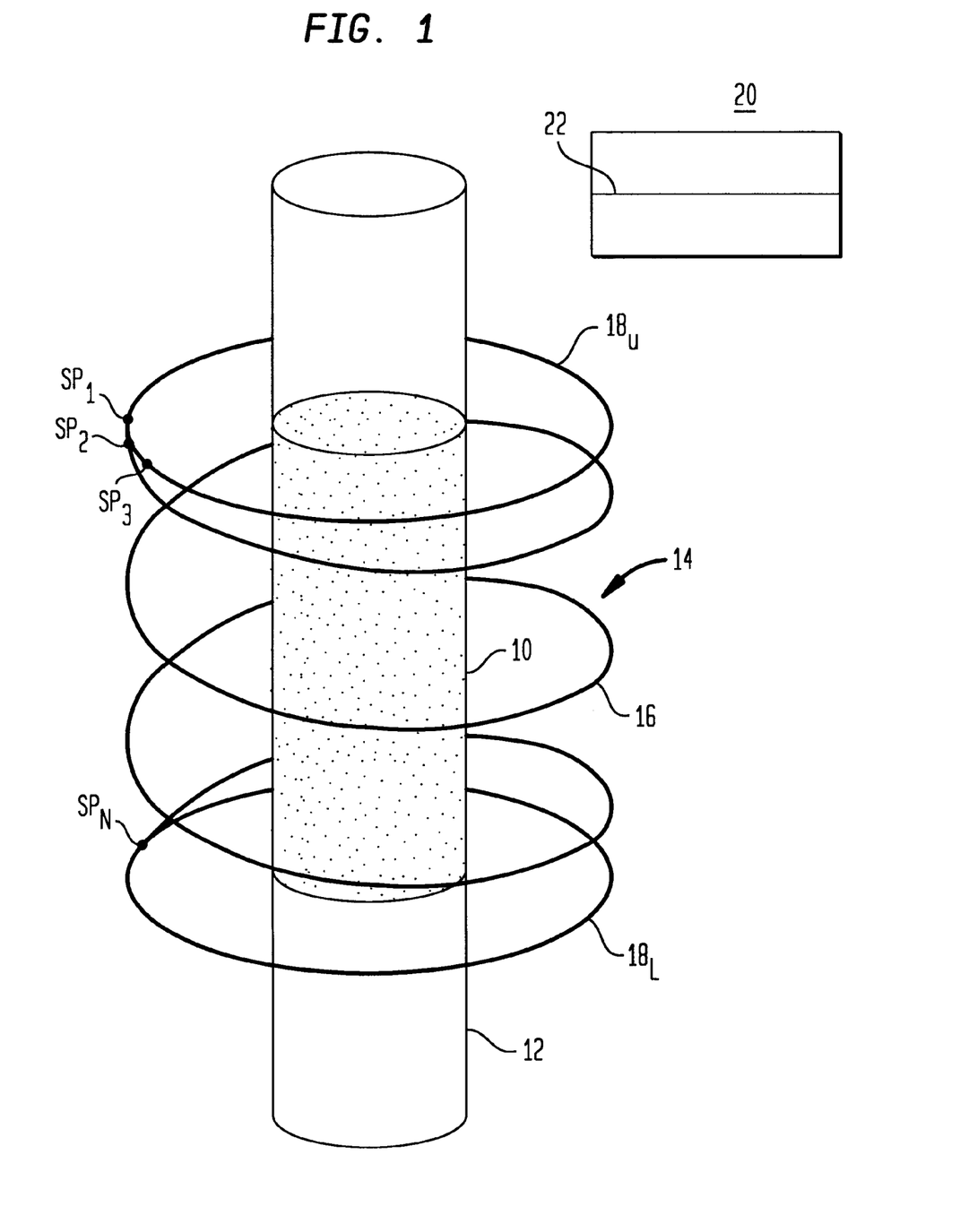
FIGS. 1 and 2, previously described, are useful for understanding the acquisition and processing of measurement data in a cone beam imaging apparatus.
Figure 5:
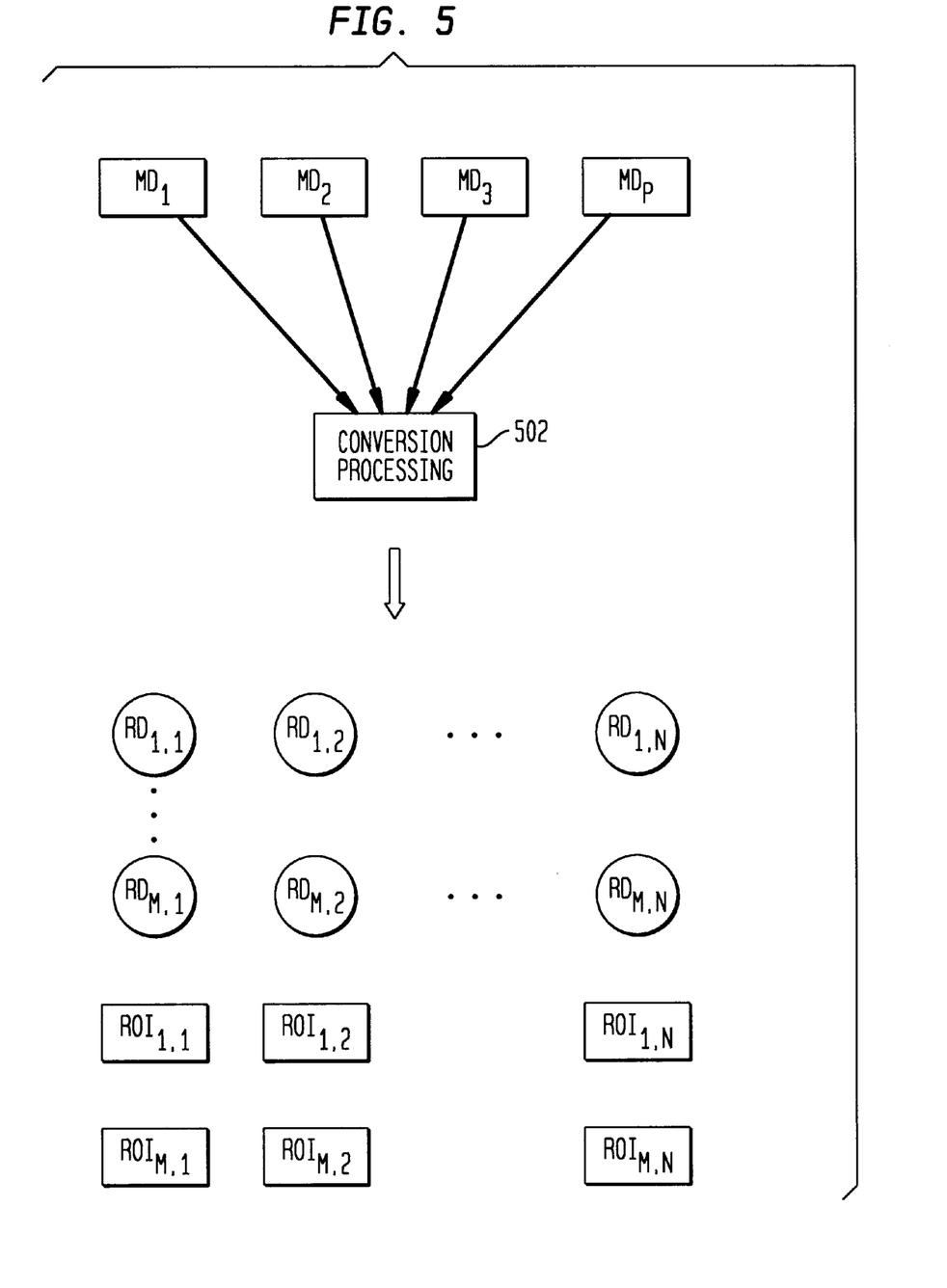
FIG. 5 is a block diagram illustrating the processing of measurement data sets MD to local ROIs of the object's parallel projections, in accordance with the principles of the present invention.

FIG. 5 is a pictorial illustration of a modification of the technique shown in FIG. 1 for processing the acquired measurement data for image reconstruction in accordance with the principles of the invention. As shown therein, sets of measurement data $MD_1$, $MD_2$, $MD_3$ ... $MD_N$ obtained at corresponding source positions $SP_1$, $SP_2$, $SP_3$ ... $SP_N$ of the radiation source along scan path 16, are processed in accordance with the previously described conversion techniques 502 to develop multiple sub-sets of Radon data $RD_{1,1}$ to $RD_{M,N}$ which, all together, contain complete Radon information of the 3D ROI of the object. The precise number of Radon data sub-sets to be developed is left up to the system designer, being a matter of various design trade-offs, however, in FIG. 5, M corresponds generally to the number of local ROIs to be reconstructed in a single ψ-plane, and N corresponds to the total number of ψ-planes upon which local ROIs are to be reconstructed. In the preferred embodiment of the invention, the use of a relative hitlist 321 is particularly advantageous for aiding the conversion of the measurement data into the sub-sets of Radon data, if, as will next be described, the local ROIs are appropriately selected.

As the conversion processing 502 results in the development of completed Radon data sub-sets $RD_{M,N}$, in accordance with the invention, it is possible for one to begin the forenoted Radon inversion processing by performing the first inversion step. Accordingly, local ROIs $ROI_{1,1}$ to $ROI_{M,N}$, which are regions-of-interest of the parallel projections of the object onto the ψ-planes of intermediate space 408, are successively developed by inversion processing of the corresponding Radon data sub-sets. After a given sub-set of Radon data has been used for developing its corresponding local ROI, that Radon data can be discarded, thereby significantly freeing-up the imaging system's computer memory.

Next, after a number of local ROI's have been developed in the ψ-planes of intermediate space 408 so as to provide 2D projection data over all the ψ-planes for a single horizontal plane (such as the z-plane 410 shown in FIG. 4), that z-plane of projection data is subjected to the second step of inversion procesing, thereby developing a corresponding z-plane image reconstruction of the object (such as z-plane 412 shown in FIG. 4). The above described steps are repeated, successively developing local ROIs and then grouping them together and performing the second step of inversion processing, thereby reconstructing an image of the 3D ROI of the object z-plane by z-plane.

Details of the above may become even clearer when one considers the problem of defining a global ROI. As previously noted, the conventional solution is to terminate the spiral scan path with two circles (as described in the forenoted U.S. Pat. No. 5,463,666). These two circles directly define the endfaces of the 3D ROI of the object, as was shown in FIG. 1 herein. The two-circles-and-a-spiral approach provides a complete scan path in the sense that it allows one to collect complete information about the enclosed part of the object. Furthermore, it is the essential feature of the circles to provide "uncontaminated" projection data at the ROI boundaries, i.e., projection data that is acquired by rays only passing through the 3D ROI of the object (no x-rays intersect the object both inside and outside of the ROI).

With the x-ray source being in the plane of the ROI boundary (as it is when it is at source positions on either of the upper or lower circle scan path portions 18 of FIG. 1), the corresponding projection data contain information from either inside or outside the ROI. The uncontaminated projection data is shown in cross-hatched shading in the bottom portion of detector data pattern 20, i.e., that portion of the data that is below line 22. Line 22 is the parallel projection of the top circle 18$_U$ of the scan path onto the detector. This allows one to cleanly separate the ROI from the rest of the object and construct the 3-D Radon transform of just the 3D ROI of the object.

Although the closed endfaces of the global ROI cannot be defined within the geometry of just the spiral portion of the scan path, the present inventors have realized that it is possible to use the spiral path to define local ROIs on the ψ-planes.

Figure 6:
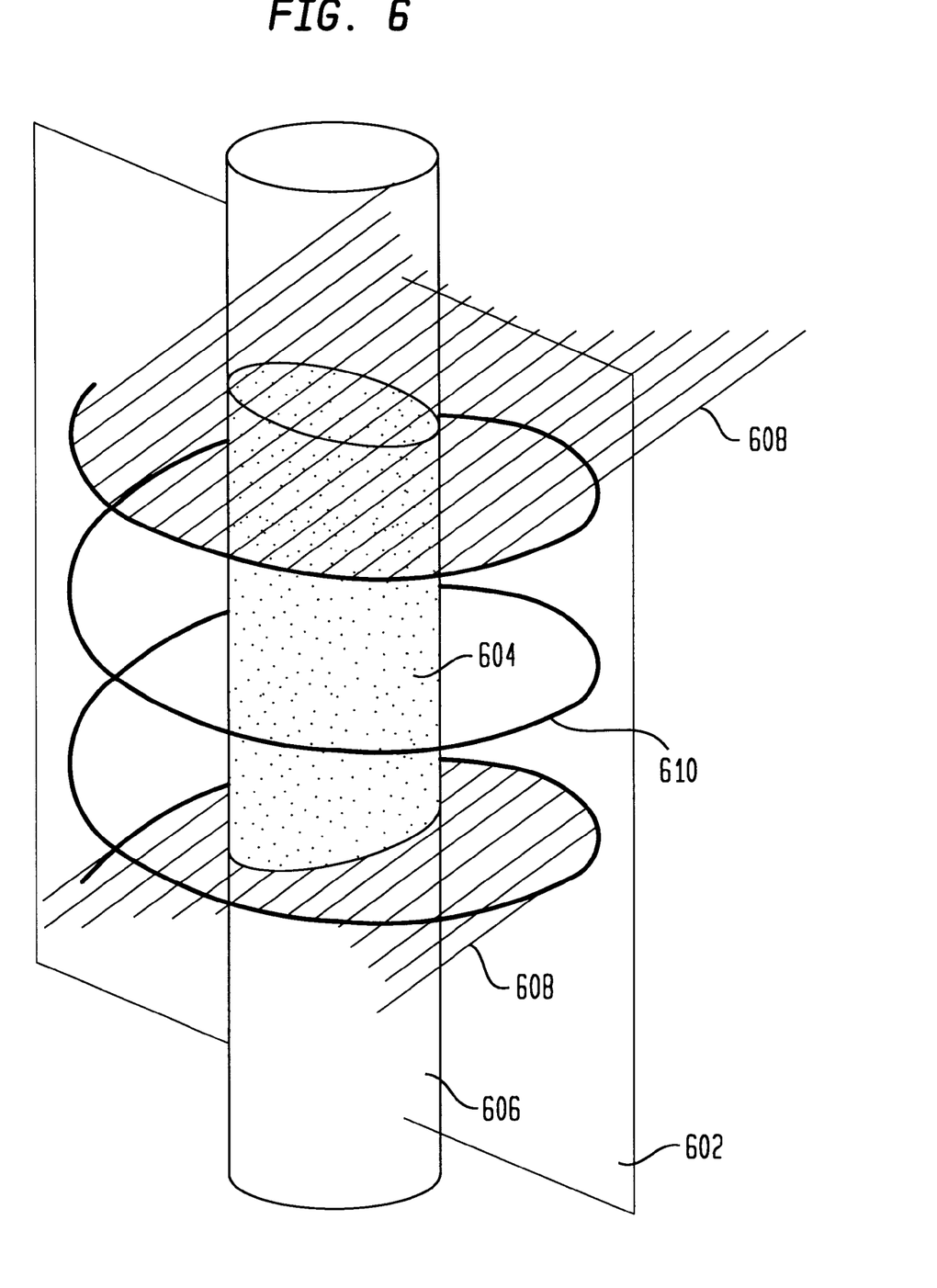
FIG. 6 illustrates how parallel projection of a spiral scan path cuts out a corresponding partial 3D volume of the object.

More specifically, as shown in FIG. 6, for each ψ-plane 602 (corresponding, i.e., to ψ-plane 402 of FIG. 4) one or more separately-shaped ROIs 604 (corresponding to a partial 3D volume 604 of object 606) can be defined, by cutting the object 606 along a parallel projection 608 of the scan path 610 onto that ψ-plane, the projection direction being normal to the ψ-plane. When the scan path comprises a spiral of uniform pitch, a whole number of such separately-shaped partial 3D volumes 604 can be defined by the scan path so that when combined, the complete volume of the 3D ROI of the object will be reconstructed. In this manner, each of the partial 3D volumes 604 corresponds to a particular local ROI on a given ψ-plane, such as local ROIs 1,1 through M,N shown in FIG. 5. In accordance with the previously described conversion and inversion processing techniques of the present invention, it is for each of these partial volumes 604 that the sub-sets 1,1 through M,N of 3D Radon data are developed.

Figure 7:
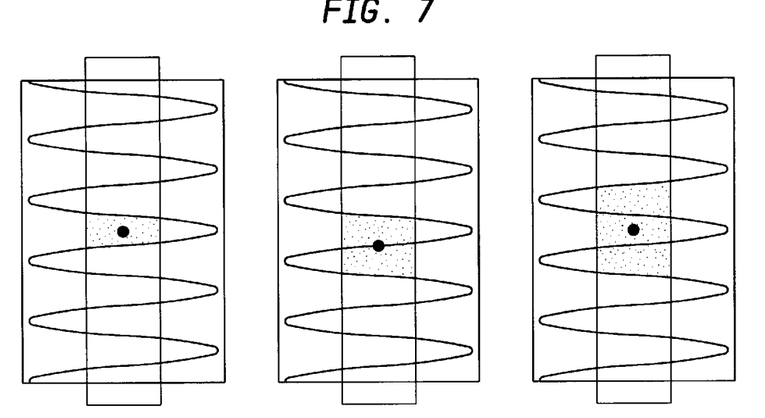
FIG. 7 shows the three smallest local ROIs which can be defined with a spiral scan path.

FIG. 7 illustrates the three smallest local ROIs which can be defined with the geometry of the spiral. Note, the ROIs are referred to as local in that they cannot all be derived from a single global 3D ROI of the object. In order to keep the size of the hitlist used in the data conversion step as small as possible, we can (as shown in FIG. 7) adjust the Radon origins so that they are centered within each local ROI. Then, the hitlist information can be re-used to assist the data conversions for each local ROI. Although one might think that it would be best to set-up the reconstruction processing so that one targets the processing of measurement data for creating the smallest of the local ROIs, as will be shown in the conjunction with FIG. 8, this may not be the most efficient implementation.

Figure 8:
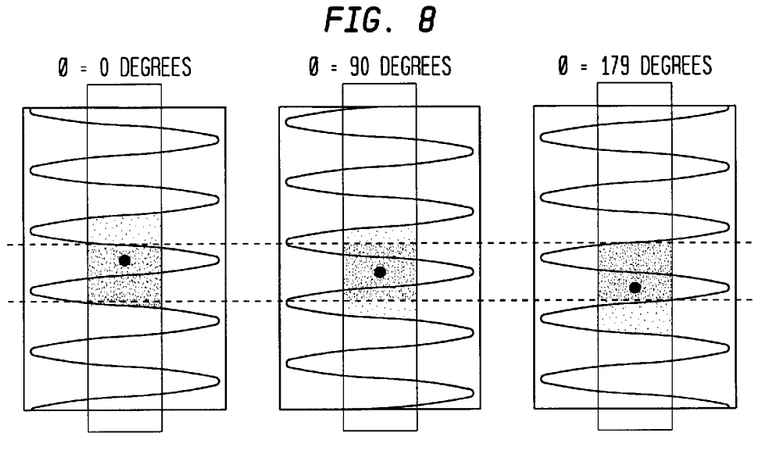
FIG. 8 illustrates how local ROIs on different (ψ-planes cover a common region along the z-axis.

Before discussion of FIG. 8, it is noted that one simple and straightforward way to define ROIs with the geometry of the spiral uses an approximation. That is, one can approximate the spiral's projection in the ψ-plane (a cosine function) by straight lines, which are then used as the upper and lower boundaries of the local ROIs. Although an approximation is used, the approximation is highly accurate for the geometry of a standard medical scanner, such as the one shown in FIG. 3. Furthermore, the accuracy increases with decreases in the size of the object.

FIG. 8 illustrates how a set of local 2D ROI's can be grouped together to extract information corresponding to a global ROI. Note, the size of the local ROI's is not the smallest, but the third smallest shown in FIG. 7, and comprises a set of 3 of the smallest sized local ROIs. Each set of ROIs is defined on a set of (ψ-planes, where ψ is in the range 0°≦ψ<180°, with three ψ-planes at ψ=0°, ψ=90° and ψ=179° being illustrated. Together the sets of local ROIs over the 180 degrees of ψ-planes cover a common range in the z-direction of the intermediate space. Within this range, shown in dark grey, the object can be reconstructed using the two-step process explained in conjunction with FIG. 4.

Figure 9:
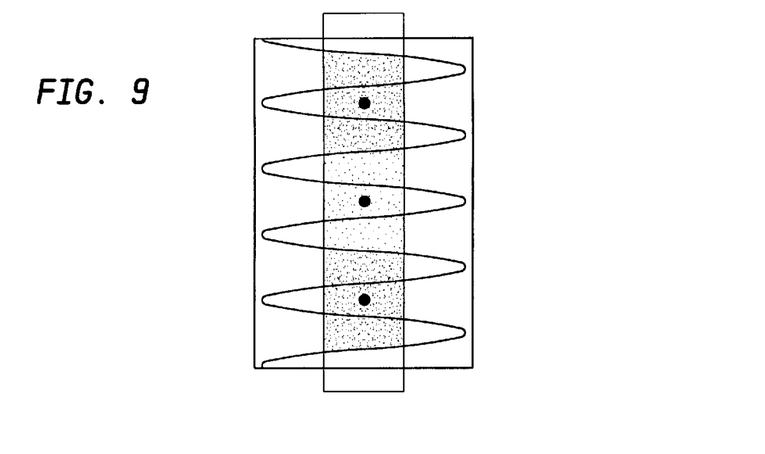
FIG. 9 illustrates how the object's projection on one (ψ-plane can be patched together by several local ROIs.

FIG. 9 illustrates how one can extend the length of the 2D projection of the object, patching together three local ROIs on one ψ-plane. If the data reconstructed at the ROI boundaries shows artifacts, one may overlap the local ROIs and use only the central portions of each ROI to achieve a better image quality.

In summary, the present invention allows piecewise reconstruction of the object, based on piecewise reconstruction of the object's parallel projections. These pieces of the object's parallel projections are referred to as local ROIs and are reconstructed from corresponding sub-sets of Radon data. In contrast, previously one had to scan the complete object, obtain its complete global Radon transform, and only then start the next reconstruction step. Piecewise image reconstruction according to the invention is helpful (e.g. for a physician in a medical scenario) because it provides more immediate access to and allows a quick check of sections of the object which are of primary importance.

The partitioning of the overall reconstruction task also reduces the required size of the computer memory. There is no need anymore to keep a large Radon space in memory for any computation. Also the size of the hitlist decreases as the local ROI size decreases.

Altogether, these benefits are very significant for a practical implementation of the exact cone beam reconstruction algorithm.

Thus, there has been shown and described a novel method and apparatus for greatly speeding up exact image reconstruction processing in a cone beam CT imaging apparatus. Many changes, modifications, variations and other uses and applications of the invention will, however, become apparent to those skilled in the art after considering this specification and its accompanying drawing, which disclose a preferred embodiment thereof.

For example, instead of a cone-shaped radiation beam, other shaped volumes may be used, such as pyramidal. Furthermore, the hitlist technique for converting the measurement data to Radon data could be modified as described in U.S. patent application Ser. No. 08/994,605 FAST CONE BEAM IMAGE RECONSTRUCTION USING A DETECTOR WEIGHT LIST, filed Dec. 19, 1997. More specifically, for each bit of acquired measurement data (i.e. for each picture element of the 2-D detector array, at each measurement position of the detector-source assembly), weight factors which determine the contribution of this bit of pixel measurement data to samples of the radial derivative of the object's 3-D Radon transform, are pre-calculated and stored. These weight factors essentially represent the point-spread function between the detector space and 3-D Radon space. The pre-calculated pixel weights are organized into what is referred to as a "detector weight list". The pre-calculated weights of the detector weight list are stored in a database which is used during run-time operation of the apparatus for supplying weight factors which are multiplied with measurement data acquired by the detector pixels so as to simply and quickly develop the multiple sub-sets 1,1 through M,N of Radon data.

All such changes, modifications, variations and other uses and applications which do not depart from the general teaching of the invention described herein, are deemed to be covered by this patent, which is limited only by the claims which follow, as interpreted in light of the foregoing description.

What is claimed is:

1. A method of operating a CT imaging apparatus having a cone beam radiation source and a 2D detector arrangement, for reconstructing an image of a 3D region of interest (ROI) of an object, comprising the following steps:

operating the source and detector arrangement at a plurality of source positions along a scan path that encircles the region of interest in the object, so as to acquire a set of measurement data at each of the source positions that is representative of radiation attenuation caused by the object as the radiation source and the detector arrangement are operated along the scan path;

conversion processing the acquired measurement data to develop multiple sub-sets of Radon data, each of the sub-sets being targeted for reconstructing a corresponding local 2D ROI in a 2D parallel projection of the object; and Radon inversion processing of multiple ones of the sub-sets that are grouped together, to develop an image reconstruction of a part of the 3D ROI in the object.

2. The method of claim 1, wherein said conversion processing develops said sub-sets of Radon data in a sampled spherical Radon space partitioned by a plurality of coaxial $\psi$-planes, and each of said targeted local 2D ROI's comprise an area on a given one of the $\psi$-planes that is defined by a 2D parallel projection of the object onto the given $\psi$-plane, and having upper and lower boundaries determined by a 2D parallel projection of the scan path that cuts through the object and onto the given $\psi$-plane.

3. The method of claim 1, wherein said Radon inversion processing step comprises first and second inversion processing steps, said first step developing said local 2D ROI's, and said second step developing said image reconstruction of said part of the object in a piecewise manner.

4. The method of claim 3, wherein the first inversion processing step comprises processing a portion of the Radon data so as to develop a 2D image on an image grid (z,r') of an intermediate space (r',$\psi$, z), and after a number of local 2D ROI's on a plurality of $\psi$-planes have been subjected to the first inversion processing step so as to be sufficient to fill up at least one z-plane of image data in the intermediate space, subjecting the at least one z-plane of image data to the second inversion processing step.

5. The method of claim 3, wherein the conversion processing step comprises using a database of pre-calculated image processing information that identifies which of the acquired measurement data should be processed to develop Radon data for the local 2D ROI's.

6. The method of claim 5, wherein the conversion processing step comprises using the database information to also identify how the acquired measurement data should be processed to develop Radon data for developing the local 2D ROI's.

7. The method of claim 5, wherein the conversion processing step comprises using the database information as a list of detector weight factors, for directly developing Radon data in a region of support for the local 2D ROI's in each of the plurality of $\psi$-planes, by multiplication of the acquired measurement data with the detector weight factors.

8. The method of claim 5, wherein the conversion processing step comprises using the database information in a relative manner so that it is re-usable for calculating sub-sets of Radon data for the local 2D ROI's in a plurality of the $\psi$-planes.

9. The method of claim 5, wherein the conversion processing step comprises using the database information for calculating the Radon data sub-set for developing a local 2D ROI in one of the $\psi$-planes, and then re-using the database information for calculating multiple sub-sets of the Radon data for developing the local 2D ROI's in multiple ones of the plurality of $\psi$-planes.

10. The method of claim 9, wherein the conversion processing step comprises using the database information useful for developing a local 2D ROI in one of the $\psi$-planes, for calculating Radon data for successively adjacent local 2D ROI's in the one $\psi$-plane.

11. The method of claim 4, wherein said first and second inversion steps each comprise a filtered backprojection step.

12. The method of claim 1, wherein said Radon inversion processing includes a first step that develops a local 2D ROI on each of the $\psi$-planes that includes a sub-area therein that spans a common portion of a plurality of the $\psi$-planes.

13. The method of claim 12, wherein the sub-areas of the local 2D ROI's that span a common portion of the $\psi$-planes, are grouped together and subjected to a second inversion processing step for developing a image reconstruction of the object in a piecewise planar manner.

14. The method of claim 12, wherein said first inversion processing step develops a plurality of 2D local ROI's which are adjacent one another on a given $\psi$-plane.

15. The method of claim 14, wherein said first inversion processing step develops said adjacent 2D local ROI's so that they are positioned on a given $\psi$-plane in an overlapped manner, and only a central portion of each 2D local ROI is subjected to said second inversion processing step, so as to reduce the occurrence of artifacts that may result from subjecting portions of each 2D local ROI that is near it's upper and lower boundaries to said second inversion processing step.

16. A scanning and data acquisition apparatus for three dimensional (3D) computerized tomography (CT) imaging of a region of interest (ROI) in an object, comprising:

an energy source for emitting energy in the form of a cone beam;

an area detector for detecting as measurement data cone beam energy after attenuation by passage through an object to be imaged;

a manipulator for movably positioning said source and detector along a scan path relative to the object, to cause irradiation of said object by said source at multiple source positions along said scan path about said object, said detector acquiring a corresponding set of measurement data at each said source position;

control means for defining the scan path as a plurality of positions on a predetermined geometric surface surrounding the object, with each of a plurality of planes that pass through the object and intersect the scan path in at least one point as well as the area detector, being useful for calculating Radon data at a given one of a plurality of Radon samples;

image reconstruction processing means including means for calculating Radon data for each of said Radon samples by processing multiple ones of the sets of measurement data, for developing image data; and display means responsive to said image data for displaying a reconstructed image of the object;

wherein said image reconstruction processing means comprises:

a conversion processor for processing the acquired measurement data to develop multiple sub-sets of Radon data, each of the sub-sets targeted for reconstructing a corresponding local 2D ROI in a 2D parallel projection of the object, and a Radon inversion processor for processing multiple ones of the sub-sets that are grouped together, to develop an image reconstruction of a part of the ROI in the object.

17. The scanning and data acquisition apparatus of claim 16, wherein said conversion processor develops said sub-sets of Radon data in a sampled spherical Radon space partitioned by a plurality of coaxial ψ-planes, with each of said targeted local 2D ROI's comprising an area on a given one of the ψ-planes that is defined by a 2D parallel projection of the object onto the given ψ-plane, and having upper and lower boundaries determined by a 2D parallel projection of the scan path that cuts through the object and onto the given ψ-plane.

18. The scanning and data acquisition apparatus of claim 16, wherein said Radon inversion processor includes a first inversion processor for developing said local 2D ROI's, and a second inversion processor for processing groups of said local 2D ROI's to develop a piecewise planar image reconstruction of the object.

19. The scanning and data acquisition apparatus of claim 18, wherein the first inversion processor processes a portion of the Radon data so as to develop a 2D image on an image grid (z,r') of an intermediate space (r',ψ, z), and after a number of local 2D ROI's on a plurality of ψ-planes have been developed so as to be sufficient to fill up at least one z-plane of image data in the intermediate space, said second inversion processor processes the at least one z-plane of image data to develop a planar image reconstruction of the object.

20. The scanning and data acquisition apparatus of claim 18, wherein the conversion processor includes a database of pre-calculated image processing information that identifies which of the acquired measurement data should be processed to develop Radon data for the local 2D ROI's.

21. The scanning and data acquisition apparatus of claim 20, wherein said database information identifies how the acquired measurement data should be processed to develop Radon data for developing the local 2D ROI's.

22. The scanning and data acquisition apparatus of claim 20, wherein said database information is a list of detector weight factors, which is used by said conversion processor for directly developing Radon data in a region of support for the local 2D ROI's in each of the plurality of ψ-planes, by multiplication of the acquired measurement data with the detector weight factors.

23. The scanning and data acquisition apparatus of claim 20, wherein said database information is used by said conversion processor in a relative manner for calculating sub-sets of Radon data for the local 2D ROI's in a plurality of the ψ-planes.

24. The scanning and data acquisition apparatus of claim 20, wherein said conversion processor uses the database information for calculating the Radon data sub-set for developing a local 2D ROI in one of the ψ-planes, and then re-uses the database information for calculating multiple sub-sets of the Radon data for developing the local 2D ROI's in multiple ones of the plurality of ψ-planes.

25. The scanning and data acquisition apparatus of claim 24, wherein said conversion processor uses the database information for developing a local 2D ROI in one of the ψ-planes, and then re-uses it for calculating Radon data for successively adjacent local 2D ROI's in the one ψ-plane.

26. The scanning and data acquisition apparatus of claim 18, wherein said first inversion processor develops a local 2D ROI on each of the ψ-planes that includes a sub-area therein that spans a common portion of a plurality of the ψ-planes.

27. The scanning and data acquisition apparatus of claim 26, wherein the sub-areas of the local 2D ROI's that span a common portion of the ψ-planes, are grouped together by a second inversion processor for developing a image reconstruction of the object in a piecewise planar manner.

* * * * *